United States Patent [19]

Hirsch et al.

[11] Patent Number: 5,318,542

[45] Date of Patent: Jun. 7, 1994

[54] SPLIT CANNULA AND PROCESS FOR THE PRODUCTION THEREOF

[75] Inventors: Christian Hirsch, Bruchköbel; Karlheinz Schlegel, Langenselbold, both of Fed. Rep. of Germany

[73] Assignee: Suddeutsche Feinmechanik GmbH, Wachtersbach, Fed. Rep. of Germany

[21] Appl. No.: 882,533

[22] Filed: May 13, 1992

[30] Foreign Application Priority Data

Jan. 8, 1992 [DE] Fed. Rep. of Germany ....... 4200255

[51] Int. Cl.$^5$ .............................................. A61M 5/00
[52] U.S. Cl. ...................................... 604/161; 604/164; 604/264; 128/898
[58] Field of Search ............... 604/160, 161, 158; 164, 604/263, 264, 280, 281; 264/146, 177.14, 177.15, 284; 72/470

[56] References Cited

U.S. PATENT DOCUMENTS

| | | | |
|---|---|---|---|
| 3,611,965 | 10/1971 | Lange | 604/160 |
| 4,243,050 | 6/1981 | Littleford | |
| 4,377,165 | 3/1983 | Luther et al. | 604/160 |
| 4,411,654 | 10/1983 | Boarini et al. | 604/161 |
| 4,772,266 | 9/1988 | Groshong | 604/160 |
| 4,776,846 | 10/1988 | Wells | 604/161 |
| 4,865,593 | 9/1989 | Ogawa et al. | 604/160 |
| 4,888,000 | 12/1989 | McQuilkin et al. | 604/160 |
| 5,167,634 | 12/1992 | Corrigan et al. | 604/160 |

FOREIGN PATENT DOCUMENTS

| | | |
|---|---|---|
| 0245837 | 11/1987 | European Pat. Off. . |
| 0435157 | 7/1991 | European Pat. Off. . |
| 2104211 | 8/1972 | Fed. Rep. of Germany . |

Primary Examiner—Stephen C. Pellegrino
Assistant Examiner—Glenn Dawson
Attorney, Agent, or Firm—Dennison, Meserole, Pollack & Scheiner

[57] ABSTRACT

A process for the production of a split cannula (10), and such a cannula having predetermined break lines (18) which run in the lengthwise direction (12) and preferably are diametrically opposite, are proposed, with the predetermined break lines (18) being produced by non-metal-cutting shaping.

5 Claims, 3 Drawing Sheets

SPLIT CANNULA AND PROCESS FOR THE PRODUCTION THEREOF

BACKGROUND OF THE INVENTION

The invention concerns a split meal cannula with at least one predetermined break line extending lengthwise, but preferably concerns a split cannula with two predetermined break lines extending lengthwise. The invention also concerns a process for the production of at least one predetermined break line extending in the lengthwise axis of a split cannula by processing of an extendable or extended tube.

So-called "split cannulas," which have predetermined break lines along the long axis of the cannula, are required in medicine, for example to introduce catheters (DE-C 2 104 211). These predetermined break lines are designed to offer the possibility, after insertion of the cannula and of the catheter that is inserted through it, for disassembling the cannula by hand into two pieces after it is pulled out. Disassembly needs to be possible with as little force as possible, while at the same time ensuring that "ripping" occurs over the entire length, in other words so that a portion of the cannula does not break off. This problem can occur, however, if the walls within the predetermined break lines do not have well-defined residual wall thicknesses. This can also cause one half of the cannula to bend, making further handling very problematical.

The predetermined break lines of known split cannulas are produced by metal-cutting processes, e.g. by milling. Because of the danger of infection from diseases such as AIDS, the user specifies that the cannulas must be free of sharp edges or burrs.

As already mentioned, the residual wall thicknesses within the predetermined break lines, which may be only a few hundredths of a millimeter thick, must also be uniform over the length of the cannula. In particular, the residual wall thicknesses of the opposite predetermined break lines must be identical, to permit easy and homogeneous ripping.

Complex manufacturing processes and regular destructive testing of finished split cannulas are needed in order to meet all these criteria. Since, in addition, manufacturing and handling are performed manually, production costs are high.

OBJECT OF THE INVENTION

The problem on which the present invention is based is that of making available a split cannula and a process for the production thereof in which a defined residual wall thickness is present over the entire length of the predetermined break line, such that discrepancies in residual wall thicknesses in the individual predetermined break lines are not present. Edges, burrs, and other imperfections on the outer surface of the split cannula are also to be excluded. Moreover, the intent is for reproducible results to be achievable with a low outlay in terms of manufacturing engineering.

According to the invention, the problem is solved, in a split metal cannula of the aforementioned type, by the fact that the predetermined break line is produced by non-metal-cutting shaping of the metal cannula. According to the invention, the preferably two predetermined break lines are not formed by milling or other metal-cutting processes, which on the one hand result in high production costs because of the necessary inspections and potential reworking, and on the other hand cannot exclude the possibility that the residual wall thicknesses will vary within one predetermined break line or from one such break line to another within a single split cannula. Instead, according to the invention, non-metal-cutting shaping causes a displacement of material, which ensures defined residual wall thicknesses. This results in the advantage that the split cannulas need to be inspected only on a sampled basis. Inspection of the outer walls themselves is also required only in isolated cases, since the non-metal-cutting shaping cannot produce roughening or formation of sharp edges on the outer surface of the finished or largely finished cannula.

Since the split cannula according to the invention has no sharp edge or burrs, the danger of injury is eliminated.

Non-metal-cutting processing also offers the advantage that even metal cannulas with very small diameters can be designed as split cannulas. Diameters less than 1 mm, for example 0.7 mm, can be designed in accordance with the invention. The process is also independent of length.

In one embodiment, the split cannula can be perforated within the predetermined break lines, allowing for even simpler disassembly of the cannula.

A process for the production of a split cannula is characterized by the fact that the predetermined break line is produced by a non-metal-cutting shaping process. In this connection, a stamping tool such as a notching die, with which an inner die running inside the tube is associated, can act along the lengthwise axis of the tube on its outer wall. This results in a defined displacement of material during the non-metal-cutting shaping process, creating small production tolerances. In particular, stamping is applied to a finished cannula, i.e. one that has been polished and, if applicable, processed to the required extent.

The process according to the invention results in a considerable reduction in the number of manufacturing steps required, and thus in improved profitability. Edges, teeth, or chips along the predetermined break line are completely eliminated.

As mentioned, the uniformity of the predetermined break lines, i.e. the residual wall thicknesses extending within them, can be increased, thus reducing the force needed to disassemble the cannula. This results in simple, reliable handling of the split cannula in medical applications.

In an embodiment of the invention, the stamping tool such as a notching die can be a knife- or blade-like tool extending along the length of the cannula, the cutting edge of which (which faces the cannula and causes the shaping) has a geometry such that two external curved sections each continue into a depression like an indentation, and then into a V-shaped projection, the height of which determines the stamping depth in the cannula wall.

Preferably, two diametrically opposite predetermined break lines are formed by rotating the tube through 180°, so that only one notching die or similarly acting element is required Alternatively, it is of course possible for a separate tool to act, simultaneously or sequentially, on each diametrically opposite line.

It is also possible to have the predetermined break lines run, with reference to the lengthwise axis of the cannula, along lines that enclose an acute angle.

Further details, advantages, and features of the invention are evident not only from the claims and the features that may be deduced from them—individually and/or in combination—but also from the following description of a preferred exemplary embodiment shown in the drawings, which is intended to illustrate the process according to the invention for the production of split cannulas.

In the drawings:

FIG. 1 shows a side view of a split cannula (10) with an obliquely ground tip (12) and, in the end region, preferably injection-embedded wings (14) and (16), which allow manipulation in order to rip the split cannula apart along predetermined break lines (18) and (20).

Although in the Figures the predetermined break lines are depicted diametrically with respect to the lengthwise axis (22) of the cannula (10), they can also be stamped in other regions in the wall of the cannula (10).

The predetermined break lines (18) and (20) create the possibility of ripping the cannula apart by pulling the wings (14) and (16) away from one another, so as thereby to remove the cannula (10) from a catheter that was previously inserted through it.

Figure 1:
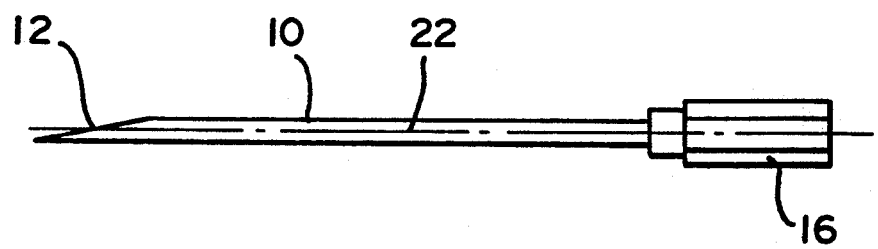
FIG. 1 shows a side view of a split cannula.
Figure 2:
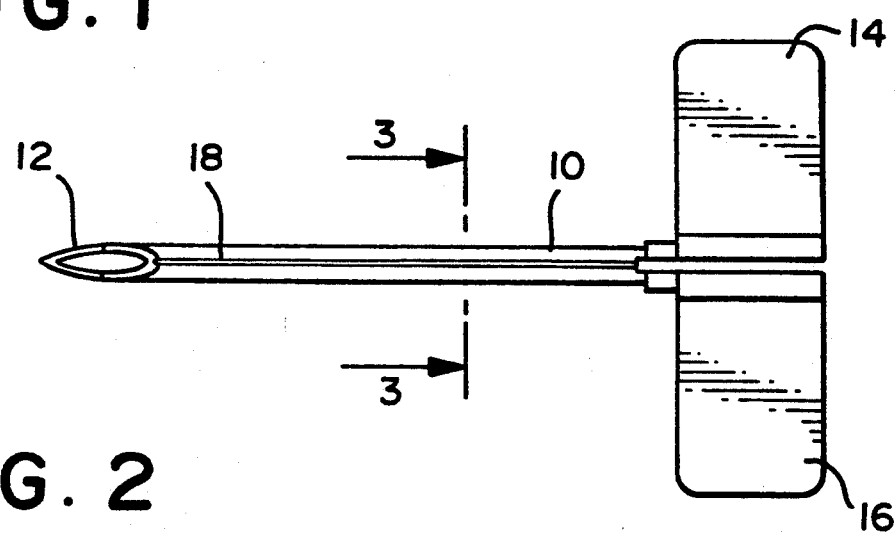
FIG. 2 shows a top view of a split cannula.
Figure 3:
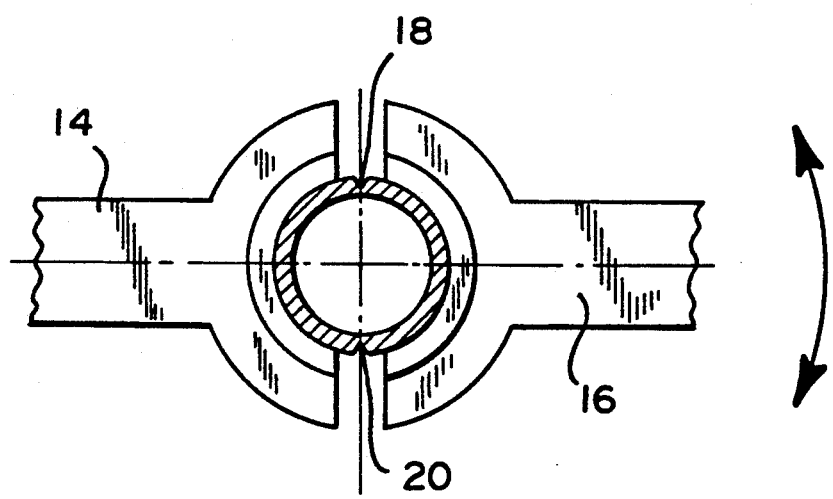
FIG. 3 shows a section along line 3—3 in FIG. 2, but at enlarged scale.
Figure 4:
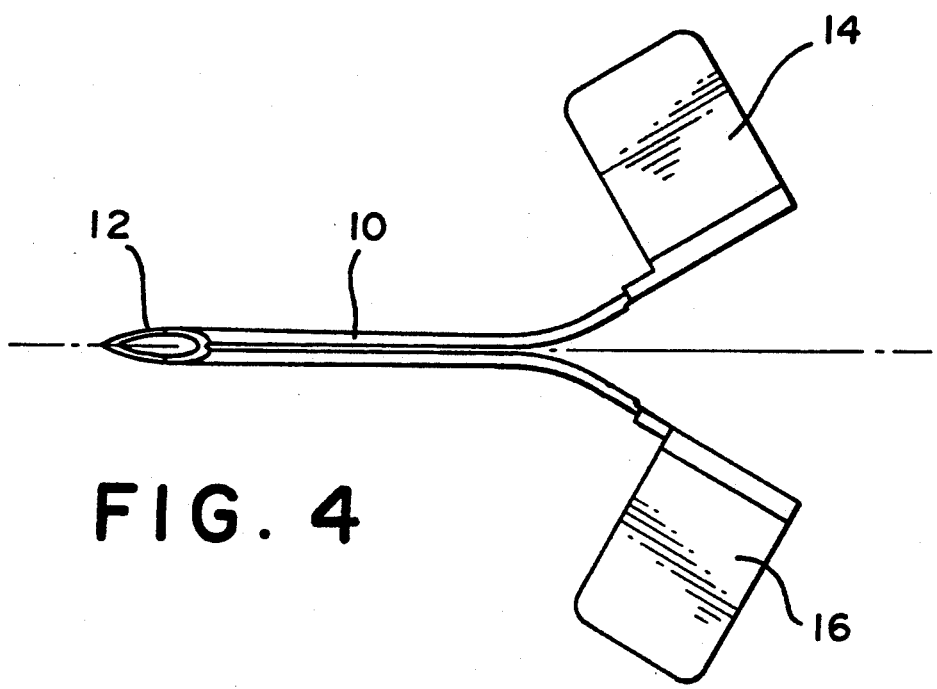
FIG. 4 shows a split cannula partly ripped apart.
Figure 5:
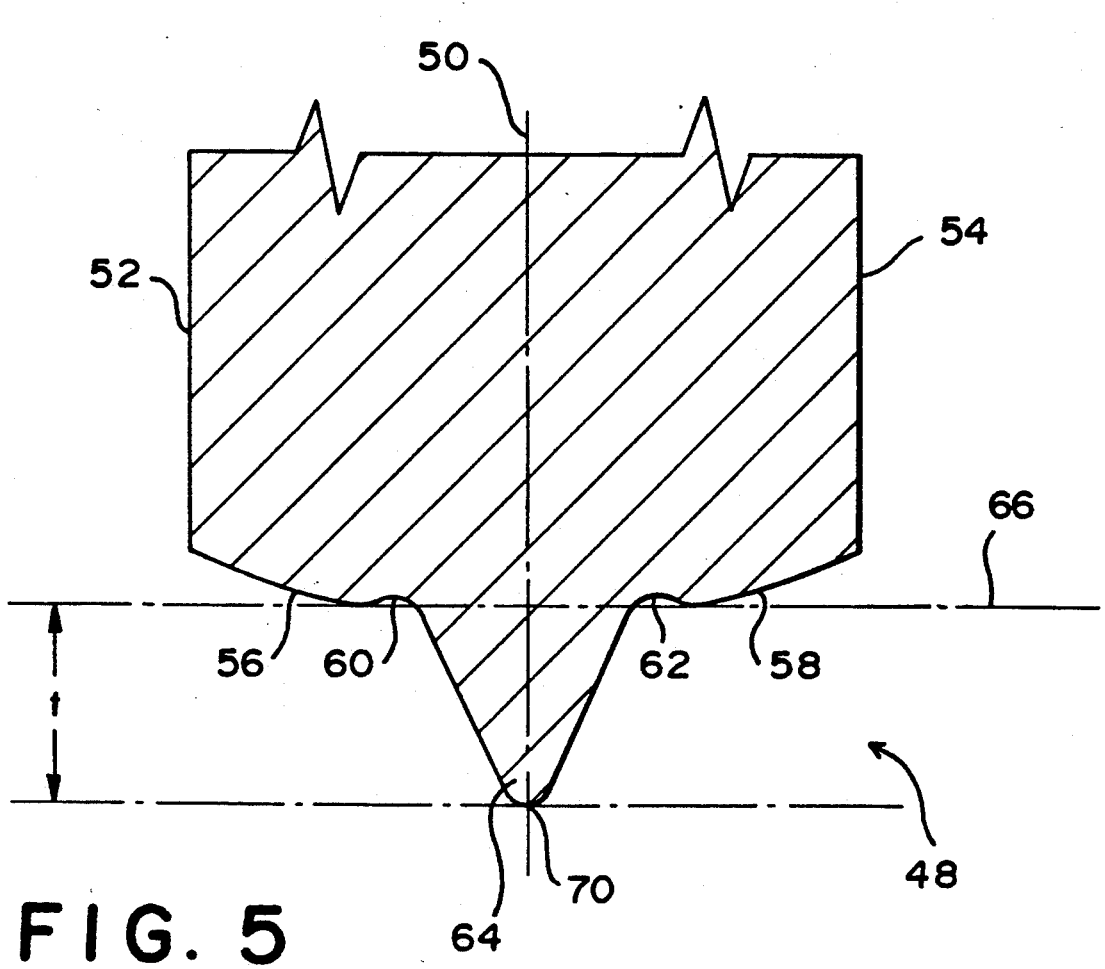
FIG. 5 shows a portion of a stamping tool.

According to the process, the procedure for creating the predetermined break lines (18) and (20) in the wall of the cannula (10) by non-metal-cutting shaping is as follows:

FIG. 5 depicts, in lengthwise section, a cutting edge region of a tool with which the predetermined break lines (18) and (20) are to be formed by non-metal-cutting shaping and, with reference to one predetermined break line, by a single stamping operation, with automatic regulation of the depth of the predetermined break line.

For this purpose the stamping edge (48) of the tool extending along the length of the cannula (10), which is referred to as the blade, has the general shape evident from FIG. 5. This means that convex elevations (56) and (58) proceed, with reference to a plane of symmetry (50), from lateral surfaces (52) and (54) of the tool, and merge via lengthwise depressions like notches (60) and (62) into an elevation (64) that is V-shaped in section. The spacing between the summits of the lateral elevations (56) and (58) and the tip of the projection (64) thus defines the depth of the predetermined break lines (18) and (20).

In order to produce the split cannula (10) with diametrically opposite predetermined break lines (18) and (20), the finished cannula (10) is positioned between fixtures (23), (24), (26), and (28). A counter-die (30) —also called a backing rod —is inserted into the cannula (10).

Stamping or notching dies (34) and (36), which extend in the lengthwise direction of the cannula (10) and taper conically toward the tip, and act on the tube wall (32) between the fixtures or retainers (23) and (26), and (24) and (28), are provided in order to stamp the predetermined break lines (18) and (20) in the wall (32) of the cannula (10) in a non-metal-cutting manner. The stamping dies (34) and (36) can have, on the cutting edge side, a geometry that corresponds to that of the stamping edge (48).

The application of force onto the stamping die (34) or (36) in the direction of the long axis (12), i.e. the center of the cannula (10), results in a displacement of material, with the penetration of the stamping die (34) or (36) being predefinable by means of stops (not illustrated). This ensures that the residual wall thickness (38) or (40), namely the distance between the inner wall (42) of the tube and the deepest point (44) or (46) of the predetermined break line (18) or (20), can be securely defined.

If a tool with the stamping edge (48) is used, a stamping depth is automatically set.

The process according to the invention consequently results in defined residual wall thicknesses (38) and (40), which guarantee that the split cannula (10) can easily be ripped apart.

Since the predetermined break lines (18) and (20) are produced by non-metal-cutting shaping, no irregularities such as edges, burrs, or the like form on the outer surface of the cannula (10), so that a smooth surface is still present. The danger of injury is thereby eliminated. In addition, no further processing of the outer wall is necessary; as a consequence, the cannula (10) can be finish-machined before it is shaped.

Non-metal-cutting shaping results in a thickening of the material directly next to the predetermined break lines (18) and (20), as is clearly evident in the drawings If, in the exemplary embodiment, two stamping tools (34) and (36) arranged diametrically opposite one another with respect to the lengthwise axis (22) are provided, the predetermined break lines (18), (20) can also be produced by only a single die (34). In this case, after creation of the predetermined break line (18), the cannula is rotated through a desired angle [alpha], preferably 180 degrees, so that the cannula (10) ends up in the position beneath the stamping die (34) at which the predetermined break line (20) is to run.

Figure 6:
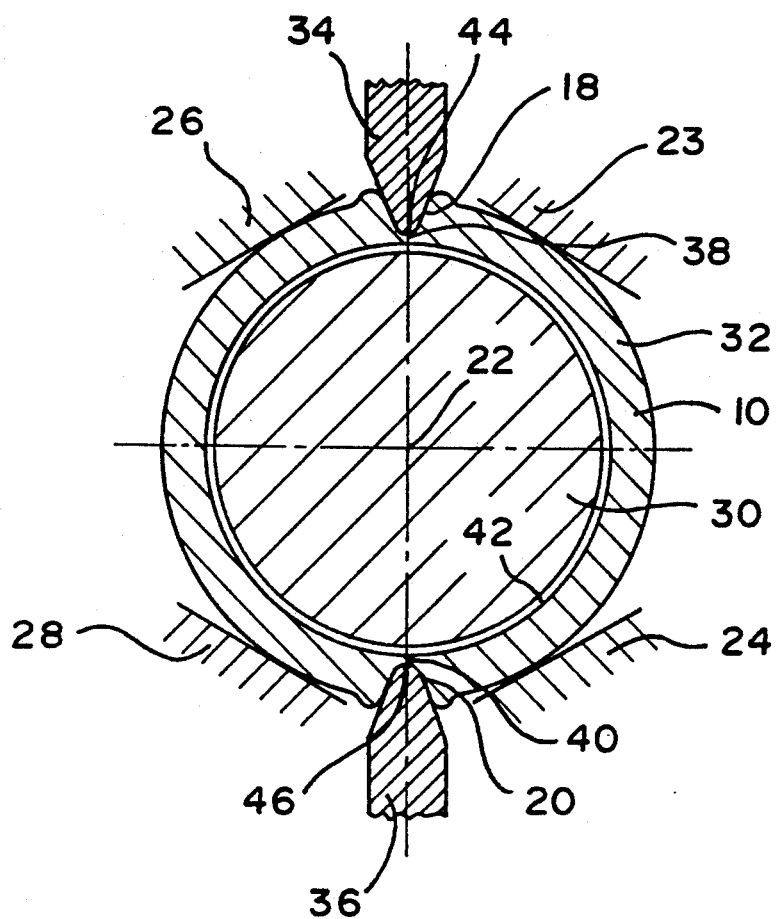
FIG. 6 shows a schematic drawing to illustrate a process for the formation of predetermined break lines in a cannula.

As FIG. 6 illustrates, the stamping tools (34) and (36) are wedge-shaped in section, with the edge running along the cannula axis (22) extending parallel to it.

Alternatively, it is possible for the edge of the tool to undulate in the lengthwise direction, so as thereby to create a variation in residual wall thickness within the predetermined break lines (18) and (20) that creates a perforation.

As FIG. 5 illustrates, the spacing between a line (66) tangent to the elevations (56) and (58), and the tip (70) of the projection (64), defines the depth t of the predetermined break line (18) or (20) to be stamped into the cannula wall (32).

I claim:

1. A process for the production of a break line running lengthwise along a split cannula by non-metal-cutting shaping, comprising the steps of introducing a counter-die lengthwise within said split cannula, positioning a stamping tool lengthwise of said split cannula exterior thereof, and forcibly engaging said stamping tool against said split cannula and in opposition to said counter-die for displacement of the material of said split cannula and formation of said break line.

2. A process for the production of break lines running lengthwise along the body of a split cannula by non-cutting shaping, comprising the steps of forming an elongate cannula body, stamping a first break line in said cannula body along the length thereof and without cutting said body, and rotating said body through a predetermined angle and stamping of a second break line in said body along the length thereof and without cutting said body.

3. A process for the production of break lines running lengthwise along the body of a split cannula by non-cutting shaping, comprising forming an elongate cannula body, and simultaneously stamping two break lines in said cannula body along the length thereof and without cutting said body.

4. A process for producing a split metal cannula comprising forming an elongate tubular metal body, and depressing a lengthwise section of said tubular body, to a constant depth and without cutting to form a break line.

5. The process of claim 4 including finishing an the outer surface of said cannula body prior to defining said break line.

* * * * *